US007634054B2

(12) United States Patent
Matoba et al.

(10) Patent No.: US 7,634,054 B2
(45) **Date of Patent: *Dec. 15, 2009**

(54) X-RAY TUBE AND X-RAY ANALYSIS APPARATUS

(75) Inventors: Yoshiki Matoba, Chiba (JP); Yutaka Ikku, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/175,768

(22) Filed: Jul. 18, 2008

(65) Prior Publication Data

US 2009/0041196 A1 Feb. 12, 2009

(30) Foreign Application Priority Data

Jul. 28, 2007 (JP) ............................ 2007-196819

(51) Int. Cl.
*G01N 23/223* (2006.01)
*H01J 35/18* (2006.01)

(52) U.S. Cl. ........................................ 378/46; 378/140

(58) Field of Classification Search ............... 378/4-50, 378/78, 86-90, 143, 140
See application file for complete search history.

(56) References Cited

U.S. PATENT DOCUMENTS 6,005,918 A 12/1999 Harris et al.
6,118,852 A 9/2000 Rogers et al.
6,487,272 B1 11/2002 Kutsuzawa
7,085,353 B2 8/2006 Yoshiyama et al.
2008/0181365 A1* 7/2008 Matoba ...................... 378/140
2009/0028297 A1* 1/2009 Matoba et al. .............. 378/140

FOREIGN PATENT DOCUMENTS

JP 8-115694 A 5/1996
JP 3062685 B 5/2000

* cited by examiner

*Primary Examiner*—Hoon Song
(74) *Attorney, Agent, or Firm*—Brinks Hofer Gilson & Lione

(57) ABSTRACT

Provided are an X-ray tube and an X-ray analysis apparatus, which can be further reduced in size as well as in weight and more efficiently detect a fluorescent X-ray and the like to increase sensitivity. The X-ray tube includes: a vacuum casing (2) having an interior in a vacuum state and a window section (1) formed of an X-ray transmission film through which an X-ray can be transmitted; an electron beam source (3) provided in the vacuum casing (2), to emit an electron beam (e); a target (T) provided in the vacuum casing (2) to be irradiated with the electron beam (e) to generate a primary X-ray and to be able to emit the generated primary X-ray through the window section (1) to an exterior sample (S); an X-ray detection element (4) provided in the vacuum casing (2) to be able to detect a fluorescent X-ray and a scattered X-ray, which are emitted from the sample (S) to be incident through the window section (1), to output a signal containing energy information of the fluorescent X-ray and the scattered X-ray; and a metal guard member (10) provided between the X-ray detection element (4) and an irradiated area of the target (T) with the electron beam (e).

6 Claims, 2 Drawing Sheets

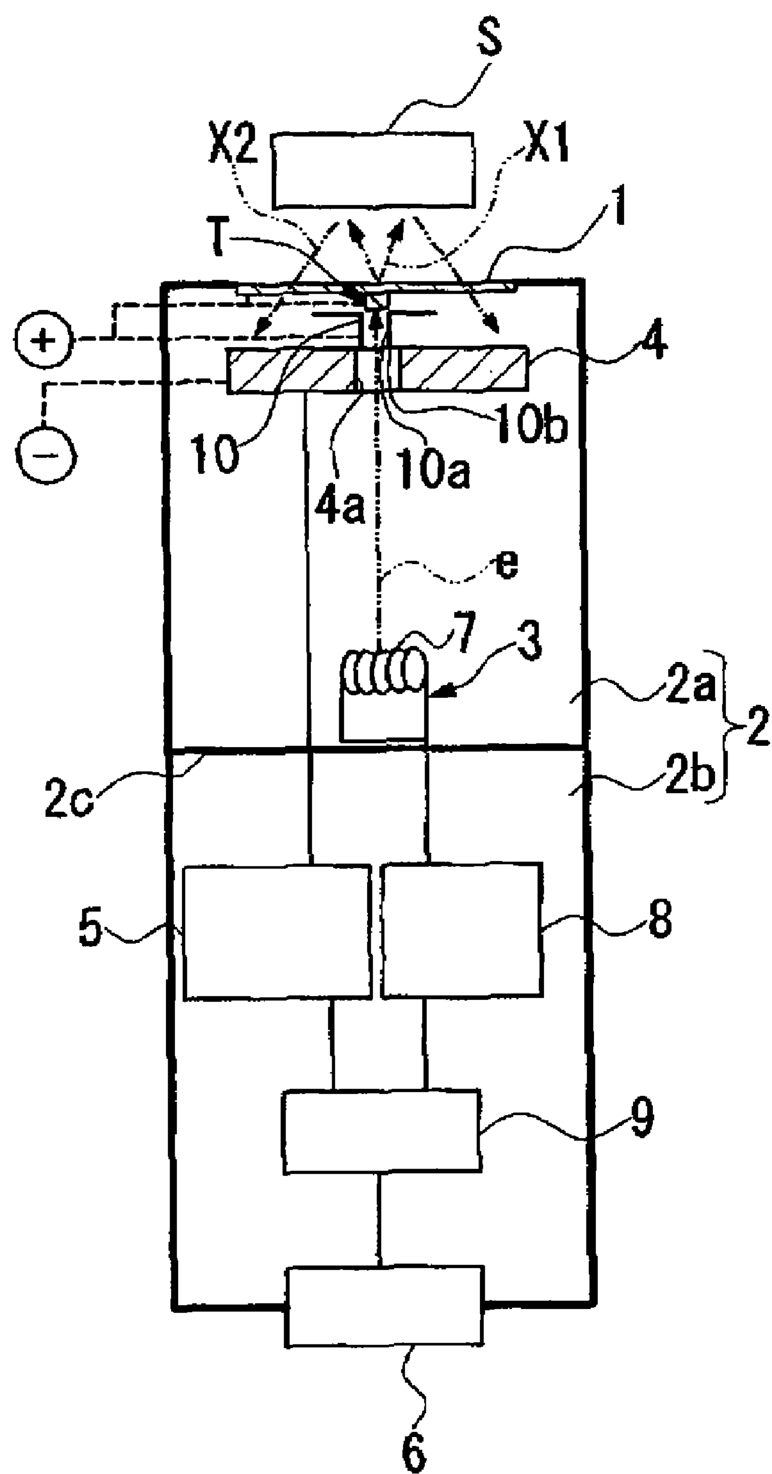
F I G. 1

X-RAY TUBE AND X-RAY ANALYSIS APPARATUS

RELATED APPLICATIONS

This application claims priority under 35 U.S.C. §119 to Japanese Patent Application No. JP2007-196819 filed on Jul. 28, 2007, the entire content of which is hereby incorporated by reference.

BACKGROUND OF THE INVENTION

1. Field of the Invention

The present invention relates to an X-ray tube and an X-ray analysis apparatus to be used for, for example, an energy-dispersive X-ray fluorescence analysis apparatus, which are suitable for small and lightweight handy X-ray analysis and portable X-ray analysis apparatuses.

2. Description of the Related Art

X-ray fluorescence analysis is used for qualitative analysis or quantitative analysis of a sample in the following manner. A primary X-ray emitted from an X-ray source is radiated to the sample. Then, a fluorescent X-ray emitted from the sample is detected by an X-ray detector to obtain a spectrum from energy of the fluorescent X-ray. The obtained spectrum is then subjected to the qualitative analysis or quantitative analysis. Since the X-ray fluorescence analysis enables the quick and non-destructive analysis of the sample, the X-ray fluorescence analysis is widely used in process and quality control or the like.

As analysis methods in the X-ray fluorescence analysis, there are a wavelength-dispersive method for splitting a fluorescent X-ray by an analyzing crystal to measure a wavelength and an intensity of the X-ray, an energy-dispersive method for detecting a fluorescent X-ray with a semiconductor detector without splitting the fluorescent X-ray to measure an energy and an intensity of the X-ray with a pulse height analyzer, and the like.

Conventionally, for example, in Japanese Patent Application Laid-Open No. 8-115694 (hereinafter, referred to as Patent Document 1), in order to increase sensitivity to the fluorescent X-ray, the following attempt has been made. An X-ray tube is provided with an extraction window for externally obtaining a fluorescent X-ray which has passed through the X-ray tube. In this manner, the X-ray tube and an X-ray detector are brought closer to a sample.

In addition, as described in Japanese Patent No. 3062685 (hereinafter, referred to as Patent Document 2), with the reduction of the X-ray tube and the X-ray analyzer in size, a handy energy-dispersive X-ray fluorescence analysis apparatus is diffused.

The above-mentioned conventional techniques still have the following problems.

For example, the X-ray analysis apparatus described in Patent Document 1 has a great effect in increasing the detection sensitivity by bringing the X-ray tube and the X-ray detector closer to the sample. However, since each of the X-ray tube and the X-ray detector has a size that is limited but equal to or larger than a certain size, a degree of the approach of the X-ray tube and the X-ray detector to the sample is also limited.

On the other hand, the conventional handy energy-dispersive X-ray fluorescence analysis apparatus is requested to be further reduced in size as well as in weight. However, since the X-ray tube and the X-ray detector occupy most of the X-ray analysis apparatus in view of volume and mass as an apparatus configuration, the conventional apparatus configuration has a limit in reduction in size and weight. Further, since the handy energy-dispersive X-ray fluorescence analysis apparatus is an open-type apparatus which directly radiates a primary X-ray to a sample in an atmosphere instead of housing and analyzing the sample in a hermetically sealed sample chamber, the amount of X-rays generated from the X-ray tube is restricted for X-ray safety reasons. Therefore, it is necessary to more efficiently detect the fluorescent X-ray from the sample.

SUMMARY OF THE INVENTION

The present invention is devised in view of the above-mentioned problems and has an object of providing an X-ray tube and an X-ray analysis apparatus, which can be further reduced in size as well as in weight and more efficiently detect a fluorescent X-ray and the like to increase sensitivity.

The present invention adopts the following configuration to solve the above-mentioned problem. Specifically, the X-ray tube according to the present invention includes: a vacuum casing having an interior in a vacuum state and a window section formed of an X-ray transmission film through which an X-ray can be transmitted; an electron beam source provided in the vacuum casing, to emit an electron beam; a target provided in the vacuum casing to be irradiated with the electron beam to generate a primary X-ray and to be able to emit the generated primary X-ray through the window section to an exterior sample; an X-ray detection element provided in the vacuum casing to be able to detect a fluorescent X-ray and a scattered X-ray, which are emitted from the sample to be incident through the window section, to output a signal containing energy information of the fluorescent X-ray and the scattered X-ray; and a guard part provided between the X-ray detection element and an irradiated area of the target with the electron beam.

Since the X-ray detection element corresponding to a constituent element of the X-ray detector is provided in the vacuum casing to be able to detect the fluorescent X-ray and the scattered X-ray which are incident through the window section. Therefore, the X-ray detection element as well as the electron beam source and the target corresponding to constituent elements of the X-ray tube are integrally housed in the vacuum casing. As a result, the whole apparatus can be further reduced in size and weight. Moreover, since the X-ray detection element is provided in the vacuum casing to be brought closer to the sample together with the target for generating the primary X-ray for the detection, excitation and detection can be extremely efficiently performed. In particular, since the application of the present invention to an open-type handy X-ray analysis apparatus enables an efficient detection, the X-ray analysis apparatus can detect the sample with high sensitivity even when the amount of generated X-rays is further suppressed. As a result, high safety can be obtained.

Further, since the guard part is provided between the X-ray detection element and the irradiated area of the target with the electron beam, the primary X-ray, secondary electrons, reflected electrons or radiant heat generated and emitted from the target can be blocked and prevented from being incident on the X-ray detection element to be noise.

Further, in the X-ray tube according to the present invention, the guard part is made of a metal and is set at one of a ground potential and a positive potential. Specifically, since the guard part made of a metal is set at one of the ground potential and the positive potential in the X-ray tube, the secondary electrons from the target can be attracted toward the guard part by the electric field to obtain a higher blocking effect.

Further, in the X-ray tube according to the present invention, the guard part is a guard member made of a metal provided between the X-ray detection element and the target. Specifically, since the guard part is a guard member made of a metal provided between the X-ray detection element and the target in the X-ray tube, radiant heat from the heat-generating target can be blocked to suppress an effect on the cooling of the X-ray detection element. Moreover, since a high degree of freedom is obtained in arrangement, shape and the like by using the metal material for the guard part, a more effective shielding effect can be obtained. For example, by forming the guard part of a material different from that of the target, for example, a heavy metal such as Cu which is suitable for shielding the X-ray detection element against the reflected electrons, the reflected electrons can be more effectively blocked.

Further, in the X-ray tube according to the present invention, the target includes a target main body corresponding to the irradiated area and a protruding wall part protruding from the target main body between the target main body and the X-ray detection element to serve as the guard part. Specifically, since the protruding wall part serving as the guard part is provided to the target itself in the X-ray tube, it is not necessary to provide the guard part as an independent member. As a result, member cost can be reduced.

The X-ray analysis apparatus according to the present invention includes: the X-ray tube according to the present invention; an analyzer for analyzing the signal; and a display section for displaying a result of analysis of the analyzer. Specifically, since the X-ray analysis apparatus is provided with the X-ray tube according to the present invention, the whole apparatus can be reduced in size.

Further, in the X-ray analysis apparatus according to the present invention, the analyzer and the display section are provided in the vacuum casing to make the X-ray analysis apparatus portable. Specifically, since the X-ray analysis apparatus is made portable by providing the analyzer and the display section in the vacuum casing in an integrated manner, a small and lightweight handy X-ray analysis apparatus, which allows the result of analysis to be instantaneously confirmed with the analyzer and the display section, can be obtained.

The present invention has the following effects.

Specifically, according to the X-ray tube and the X-ray analysis apparatus according to the present invention, the X-ray detection element is provided in the vacuum casing to be able to detect the fluorescent X-ray and the scattered X-ray which are incident through the window section. Therefore, the whole apparatus can be further reduced in size as well as in weight. At the same time, excitation and detection can be more efficiently performed. Moreover, since the guard part is provided between the X-ray detection element and the electron beam irradiated area of the target, the primary X-ray, the secondary electrons, the reflected electrons, the radiant heat and the like from the target can be blocked to suppress an adverse effect on the X-ray detection element. As a result, a highly accurate measurement can be obtained. In particular, when the present invention is applied to an open-type handy X-ray analysis apparatus, the X-ray can be detected with high sensitivity even if the amount of generated X-rays is suppressed. Thus, high safety can be obtained.

BRIEF DESCRIPTION OF THE DRAWINGS

In the accompanying drawings:

FIG. 1 is an overall schematic configuration diagram of an X-ray analysis apparatus according to a first embodiment of the present invention;

DETAILED DESCRIPTION OF THE PREFERRED EMBODIMENTS

Figure 2:
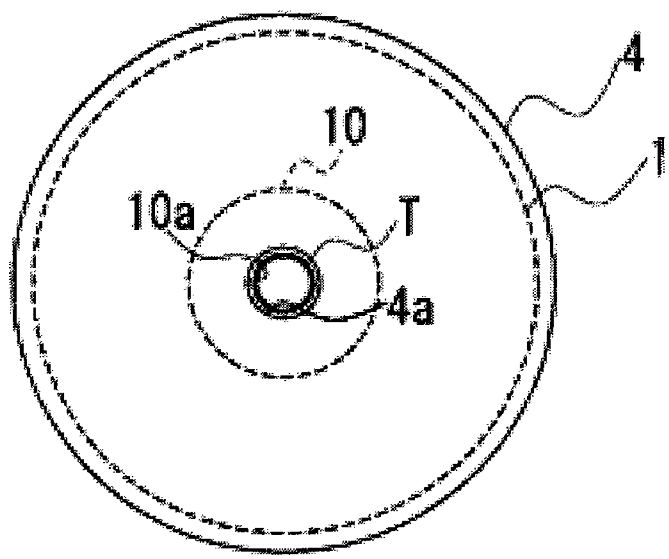
FIG. 2 is an arrangement plan illustrating a positional relation between an X-ray detection element, a metal guide member, a target, and a window section, viewed directly above from the X-ray detection element, according to the first embodiment.

Hereinafter, a first embodiment of an X-ray tube and an X-ray analysis apparatus according to the present invention is described referring to FIGS. 1 and 2. In each of the drawings referred to in the following description, scale size is appropriately changed to show each member in an identifiable or easily identified manner.

The X-ray analysis apparatus according to this first embodiment is a portable (handy) energy-dispersive X-ray fluorescence analysis apparatus. As illustrated in FIG. 1, the X-ray analysis apparatus includes a vacuum casing 2, an electron beam source 3, a target T, an X-ray detection element 4, a metal guard member (guard part) 10, an analyzer 5, and a display section 6. A part of the interior of the vacuum casing 2 is in a vacuum state. The vacuum casing 2 has a window section 1 formed of an X-ray transmission film which can transmit an X-ray therethrough. The electron beam source 3 is provided in the vacuum casing 2 to emit an electron beam e. The target T is provided in the vacuum casing 2 to generate a primary X-ray X1 when irradiated with the electron beam e. Simultaneously, the target T emits the generated primary X-ray 1 through the window section 1 to a sample S in the exterior. The X-ray detection element 4 is provided in the vacuum casing 2 to be able to detect a fluorescent X-ray and a scattered X-ray X2 which are emitted from the sample S to be incident on the X-ray detection element 4 through the window section 1. The X-ray detection element 4 outputs a signal containing energy information of the fluorescent X-ray and the scattered X-ray X2. The metal guard member 10 is provided between the X-ray detection element 4 and an irradiated area of the target T with the electron beam e. The analyzer 5 analyzes the signal. The display section 6 displays the result of analysis by the analyzer 5. The X-ray tube includes, as main components, the vacuum casing 2, the electron beam source 3, the target T, the X-ray detection element 4, and the metal guard member 10.

The vacuum casing 2 includes a front housing section 2*a* whose interior is in a vacuum state and a rear housing section 2*b* whose interior is in an atmospheric state, which is separated from the front housing section 2*a* by a partition wall 2*c*.

The window section 1 is formed of, for example, a Be (beryllium) foil as the X-ray transmission film. A primary filter corresponding to a thin metal film or a thin metal plate made of Cu (copper), Zr (zirconium), Mo (molybdenum) or the like, selected according to the sample S, may be attached on a front face of the window section 1. The window section 1 and the target T are set at a ground potential or a positive potential to draw back secondary electrons generated and emitted by an interaction between the electron beam e incident on the target T and the target T. Since the secondary electrons normally have the energy of only about several eV, the ground potential or the positive potential is set to form an electric field which is equal to or higher than the energy of the secondary electrons.

The electron beam source 3 includes a filament 7 serving as a cathode and a current/voltage control section 8 for controlling a voltage (tube voltage) between the filament 7 and the target T serving as an anode and a current (tube current) of the electron beam e. The electron beam source 3 generates an X-ray generated in the following manner as a primary X-ray. Thermions (electron beam) generated from the filament 7 serving as the cathode are accelerated by the voltage (for example, at 50 keV) applied between the filament 7 and the target T serving as the anode to collide against the target T. As a result, the X-ray is generated as the primary X-ray.

A carbon nanotube may be used as the cathode in place of the filament 7.

As the target T, for example, W (tungsten), Mo (molybdenum), Cr (chromium), Rh (rhodium) or the like is used. The target T is placed in proximity to or in contact with the window section 1.

The X-ray detection element 4 is a semiconductor detection element such as an Si (silicon) element which is, for example, a PIN diode. When a single X-ray photon is incident on the X-ray detection element 4, the X-ray detection element 4 generates a current pulse corresponding to the single X-ray photon. A momentary current value of the current pulse is proportional to the energy of the incident fluorescent X-ray.

The X-ray detection element 4 is located at an area between the filament 7 of the electron beam source 3 and the target T, as illustrated in FIGS. 1 and 2. The X-ray detection element 4 has a transmission hole 4*a* through which the electron beam e can be transmitted. The target T is provided just below the transmission hole 4*a* in proximity thereto. A light-receiving surface of the X-ray detection element 4 is provided around the target T.

The X-ray detection element 4 is set to be kept at a constant temperature by a cooling mechanism (not shown; for example, a cooling mechanism using liquefied nitrogen as a coolant or a cooling mechanism using a Peltier element). The X-ray detection element 4 can ensure its proper performance by being cooled at about −30 to −100 degrees.

The metal guard member 10 is provided between the irradiated area of the target T with the electron beam e and the X-ray detection element 4 to prevent the primary X-ray X1, secondary electrons, reflected electrons, and radiant heat from the target T from entering the X-ray detection element 4. The metal guard member 10 is fixed to the vacuum casing 2 by a support (not shown). The metal guard member 10 is an annular member having a transmission hole 10*a* for the electron beam e in the center to allow the electron beam e to be transmitted therethrough. The support serves not only to support the metal guard member 10 but also to release the secondary electrons and the radiant heat.

The metal guard member 10 in this first embodiment has a cylindrical part 10*b*, whose interior serves as the transmission hole 10*a*, provided in the center. The cylindrical part 10*b* may also be inserted into the transmission hole 4*a* of the X-ray detection element 4. The size and the shape of the metal guard member 10 are determined according to the positional relation between the target T and the X-ray detection element 4 and the like to prevent the reflected electrons linearly emitted from the target T from being incident on the X-ray detection element 4. In this manner, the metal guard member 10 is provided in a path of the reflected electrons to allow the reflected electrons to be blocked. The metal guard member 10 is formed of a heavy metal such as Cu. As in the case of the window section 1 and the target T, the metal guard member 10 is set at the ground potential or the positive potential.

By setting the X-ray detection element 4 at a negative potential, thermions (electron beam e) can be prevented from being incident on the X-ray detection element 4.

The filament 7, the target T, the X-ray detection element 4, and the metal guard member 10 are provided in the front housing section 2*a* of the vacuum casing 2.

The analyzer 5 described above corresponds to an X-ray signal processing section. The analyzer 5 is a multi-channel pulse height analyzer for converting the current pulse generated from the X-ray detection element 4 into a voltage pulse, amplifying the voltage pulse to obtain a signal, and obtaining a pulse height of the voltage pulse from the signal to generate an energy spectrum.

The current/voltage control section 8 and the analyzer 5 are connected to a CPU 9. Various controls are performed on the current/voltage control section 8 and the analyzer 5 by setting.

The display section 6 is, for example, a liquid crystal display device. The display section 6 is connected to the CPU 9 to enable not only the display of the result of analysis such as energy spectrum but also various screen displays according to setting.

The analyzer 5, the current/voltage control section 8, and the CPU 9 are provided in the rear housing section 2*b* of the vacuum casing 2, whereas the display section 6 is provided to locate its display face on the outer surface of the rear housing section 2*b*. Specifically, the analyzer 5 and the display section 6 are provided in the vacuum casing 2 in an integrated manner.

Each of the structures described above, which requires a power supply and potential setting, is connected to a power source section (not shown).

As described above, in this first embodiment, the X-ray detection element 4 is provided in the vacuum casing 2 to be able to detect the fluorescent X-ray and the scattered X-ray X2 incident through the window section 1. Therefore, the X-ray detection element 4 as well as the electron beam source 3 and the target T are integrally housed in the vacuum casing 2. As a result, the whole apparatus can be further reduced in size and weight. Moreover, since the X-ray detection element 4 is provided in the vacuum casing 2 to be brought closer to the sample S together with the target T for generating the primary X-ray X1 for the detection, extremely efficient excitation and detection are made possible. In particular, since the application of the present invention to the open-type handy X-ray analysis apparatus enables an efficient detection, the X-ray analysis apparatus can detect the sample with high sensitivity even when the amount of generated X-rays is further suppressed. As a result, high safety can be obtained.

Further, since the light-receiving face of the X-ray detection element 4 is provided around the target T, the primary X-ray X1 from the target T can be efficiently incident on the sample S when the sample S is analyzed in proximity to the window section 1. Further, the fluorescent X-ray or the like generated from the sample S can be efficiently detected by the X-ray detection element 4 provided around the target T (specifically, in proximity to the window 1).

Further, since the electron beam e is radiated to the target T through the transmission hole 4*a* of the X-ray detection element 4 provided between the electron beam source 3 and the target T, the electron beam e can be radiated to the target T after being focused by the transmission hole 4*a*.

Since the metal guard member 10 is provided between the X-ray detection element 4 and the irradiated area of the target T with the electron beam e, the secondary electrons and the reflected electrons, which are generated and emitted from the target T corresponding to the X-ray generating section, can be blocked and prevented from being incident on the X-ray detection element 4 to be noise. At the same time, the radiant heat from the heat-generating target T can be blocked to suppress an effect on the cooling by the X-ray detection element 4.

Further, since the metal guard member 10 is set at the ground potential or the positive potential, the secondary electrons from the target T can be attracted to the metal guard member 10 by the electric field. As a result, a higher blocking effect can be obtained.

Further, since the target T and the window section 1 are set at the ground potential or the positive potential, the secondary electrons from the target T are drawn back to the target T and the window section 1 by the electric field. As a result, the secondary electrons can be prevented from being incident on the X-ray detection element 4.

Moreover, since the X-ray analysis apparatus is formed as a portable X-ray analysis apparatus which includes the analyzer 5 and the display section 6 provided in the vacuum casing 2 in the integrated manner, the X-ray analysis apparatus can be constituted as a small and lightweight handy X-ray analysis apparatus which allows the result of analysis to be instantaneously recognized with the analyzer 5 and the display section 6.

Figure 3:
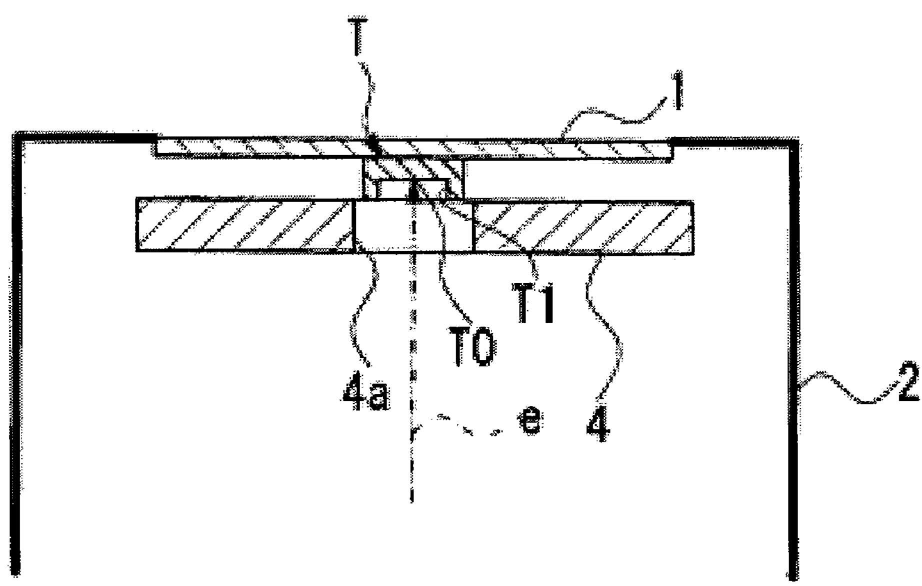
FIG. 3 is a schematic sectional view of a main part of the X-ray analysis apparatus according to a second embodiment of the present invention.

Next, the X-ray tube and the X-ray analysis apparatus according to a second embodiment of the present invention are described referring to FIG. 3. In the following description of the second embodiment, the same components as those described in the first embodiment are denoted by the same reference numerals, and the description thereof is herein omitted.

The second embodiment differs from the first embodiment in the following point. Although the metal guide member 10 is provided between the target T and the X-ray detection element 4 in the first embodiment, a protruding wall part (guard part) T1 is provided to the target T itself to serve as a guard part in the X-ray tube and the X-ray analysis apparatus in the second embodiment, as illustrated in FIG. 3. Specifically, the target T in the second embodiment includes a target main body T0 corresponding to an irradiated area with the electron beam e, and the protruding wall part T1 protruding from an outer edge part of the target main body T0 between the target main body and the X-ray detection element 4, which serves as a guard part.

The target main body T0 is formed in a disc-like shape, whereas the protruding wall part T1 is a convex body protruding from the outer edge part of the target main body T0 between the target main body and the X-ray detection element 4. The protruding wall part T1 may also be inserted into the transmission hole 4*a* of the X-ray detection element 4.

As described above, in the X-ray tube and the X-ray analysis apparatus in the second embodiment, the target T itself is provided with the protruding wall part T1 serving as a guard part which can block the secondary electrodes and the reflected electrodes. Therefore, since the guard part is not required to be provided as an independent member, member cost can be reduced.

The technical scope of the present invention is not limited to the above-mentioned embodiments. Various changes are possible without departing from the scope of the present invention.

For example, although the energy-dispersive X-ray fluorescence analysis apparatus is used in each of the above embodiments, the present invention may also be applied to an X-ray fluorescence analysis apparatus using other analysis methods, for example, to a wavelength-dispersive X-ray fluorescence analysis apparatus.

Moreover, although the present invention is suitable for the handy X-ray analysis apparatus as in the embodiments described above, the present invention may be applied to a stationary X-ray analysis apparatus. For example, the X-ray analysis apparatus may be constituted as a stationary X-ray analysis apparatus including the X-ray tube, which includes the vacuum casing 2, the electron beam source 3, the target T, and the X-ray detection element 4, and the analyzer 5, a control system, the display section 6, and the like as members separate from the X-ray tube.

What is claimed is:

1. An X-ray tube comprising:

a vacuum casing including an interior in a vacuum state and a window section formed of an X-ray transmission film through which an X-ray is transmitted;

an electron beam source provided in the vacuum casing to emit an electron beam;

a target irradiated with the electron beam to generate a primary X-ray and to emit the generated primary X-ray through the window section to an exterior sample, the target being provided on the window section and having an outer diameter smaller than that of the window section;

an X-ray detection element provided in the vacuum casing to detect a fluorescent X-ray and a scattered X-ray, the fluorescent X-ray and the scattered X-ray being emitted from the sample to be incident through the window section, to output a signal containing energy information of the fluorescent X-ray and the scattered X-ray; and a guard part provided between the X-ray detection element and an irradiated area of the target with the electron beam.

2. An X-ray tube according to claim 1, wherein the guard part is made of a metal and is set at one of a ground potential and a positive potential.

3. An X-ray tube according to claim 1, wherein the guard part is a guard member made of a metal provided between the X-ray detection element and the target.

4. An X-ray tube according to claim 1, wherein the target includes a target main body corresponding to the irradiated area and a protruding wall part protruding from the target main body between the target main body and the X-ray detection element to serve as the guard part.

5. An X-ray analysis apparatus comprising:

the X-ray tube according to claim 1;

an analyzer for analyzing the signal; and a display section for displaying a result of analysis of the analyzer.

6. An X-ray analysis apparatus according to claim 5, wherein the analyzer and the display section are provided in the vacuum casing to make the X-ray analysis apparatus portable.

* * * * *